United States Patent [19]

Busch et al.

[11] Patent Number: 5,338,846

[45] Date of Patent: Aug. 16, 1994

[54] PROCESS FOR PREPARING ARYL PIPERAZINYL-HETEROCYCLIC COMPOUNDS WITH A PIPERAZINE SALT

[75] Inventors: Frank R. Busch, Gales Ferry; Paul Bowles, Groton; Douglas John, New London; Meldrum Allen, Uncasville; Sabeto A. DiRoma; Dennis M. Godek, both of Glastonbury, all of Conn.

[73] Assignee: Pfizer Inc., New York, N.Y.

[21] Appl. No.: 49,905

[22] Filed: Apr. 20, 1993

Related U.S. Application Data

[63] Continuation-in-part of Ser. No. 936,179, Aug. 26, 1992, Pat. No. 5,206,366, and Ser. No. 939,204, Sep. 1, 1992.

[51] Int. Cl.$^5$ .................. C07D 417/06; C07D 413/06
[52] U.S. Cl. ..................................... 544/368
[58] Field of Search ........................ 544/368

[56] References Cited

U.S. PATENT DOCUMENTS

| | | | |
|---|---|---|---|
| 4,558,060 | 12/1985 | Caignard et al. | 544/368 |
| 4,610,988 | 9/1986 | Davis et al. | 544/368 |
| 4,831,031 | 5/1989 | Lowe, III et al. | 544/368 |
| 4,883,795 | 11/1989 | Lowe, III et al. | 544/368 |
| 5,206,366 | 4/1993 | Bowles | 544/368 |

OTHER PUBLICATIONS

Yevich, J. P. et al., "Synthesis and Biological Evaluation of 1-(1,2-Benzisothiazol-3-yl)-and (1,2-Benzisoxazol-3-yl)piperazine Derivatives as Potential Antipsychotic Agents," *J. Med. Chem.*, 29, No. 3, pp. 359–369 (1986).

*Primary Examiner*—Cecilia Tsang
*Attorney, Agent, or Firm*—Peter C. Richardson; Paul H. Ginsburg; Philip C. Strassburger

[57] ABSTRACT

A process for preparing a compounds of the formula

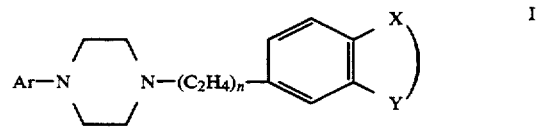

or a pharmaceutically acceptable acid addition salt thereof, which comprises reacting a piperazine salt of the formula

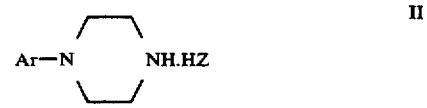

with an alkyl halide containing compound of the formula

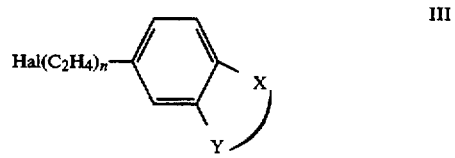

in water with a reagent to neutralize the hydrohalic acid and heating the mixture under conditions which are suitable to effect the coupling of said piperazine salt with said alkyl halide containing compound.

19 Claims, No Drawings

PROCESS FOR PREPARING ARYL PIPERAZINYL-HETEROCYCLIC COMPOUNDS WITH A PIPERAZINE SALT

This is a continuation-in-part of U.S. patent application Ser. No. 07/936,179 filed Aug. 26, 1992 (U.S. Pat. No. 5,206,366), and a continuation-in-part of U.S. patent application Ser. No. 07/939,204 filed Sep. 1, 1992.

BACKGROUND OF THE INVENTION

The present invention is directed to a novel process for preparing arylpiperazinyl-ethyl (or butyl)-heterocyclic compounds and their pharmaceutically acceptable acid addition salts by reacting a piperazine salt with an alkyl halide.

U.S. Pat. No. 4,831,031 indicates that arylpiperazinyl-ethyl (or butyl)heterocyclic compounds may be prepared by reacting an N-arylpiperazine with a fused bicyclic compound. This coupling reaction is generally conducted in a polar solvent (such as a lower alcohol, dimethylformamide or methylisobutylketone) and in the presence of a weak base, and preferably the reaction is in the further presence of a catalytic amount of sodium iodide and a neutralizing agent for hydrochloride such as sodium carbonate.

Yevich et al., *J. Med. Chem.*, 29, No. 3, pp. 359–369 (1986), relates to a method of producing 1-(1,2-benzisothiazol-3-yl)- and (1,2-benzisoxazol-3-yl)piperazine derivatives. Several reaction schemes are disclosed, including reaction schemes wherein coupling occurs in a free base.

Copending U.S. patent application Ser. No. 07/936,179 filed Aug. 26, 1992 (U.S. Pat. No. 5,206,366), relates to a process of preparing arylpiperazinyl-ethyl (or butyl)-heterocyclic compounds by reacting a monosubstituted piperazine with an alkyl halide.

Copending U.S. patent application Ser. No. 07/939,204 filed Sep. 1, 1992, relates to 5-(2-(4-(1,2-benzisothiazol-3-yl)-1-piperazinyl)ethyl)-6-chloro-1,3-dihydro-2H-indol-2-one hydrochloride monohydrate, and a process for preparing that compound comprising reacting anhydrous 5-(2-(4-(1,2-benzisothiazol-3-yl)-1-piperazinyl)ethyl)-6-chloro-1,3-dihydro-2H-indol-2-one with aqueous hydrochloric acid.

All of the documents and copending patent applications cited herein, including the foregoing, are hereby incorporated in this application in their entireties.

The present invention relates to a new and useful process for effecting coupling reactions of piperazine salt derivatives with alkyl halide derivatives that provide aryl piperazinyl-ethyl (or butyl)-heterocyclic compounds in greater yields than known methods. In the present invention, the coupling reaction is conducted in water. This aqueous based coupling process is not only more efficient but has a much lower environmental burden since the handling and disposal of organic solvents are eliminated. This process has not shown formation of byproducts and does not require special isolation procedures, e.g., extractions, distillations and recrystallizations. Also, the present invention results in a decrease in lumping during the coupling reaction.

SUMMARY OF THE INVENTION

The present invention relates to a novel process of preparing compounds of the formula

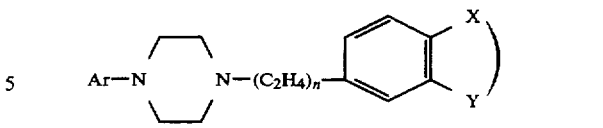

and the pharmaceutically acceptable acid addition salts thereof, wherein Ar is naphthyl optionally substituted with one to four substituents independently selected from fluoro, chloro, trifluoromethyl, methoxy, cyano and nitro; quinolyl; isoquinolyl quinazolyl; 6-hydroxy-8-quinolyl; benzoisothiazolyl and an oxide or dioxide thereof, each optionally substituted with one or more substituents independently selected from fluoro, chloro, trifluoromethyl, methoxy, cyano, and nitro; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; and phthalazinyl;

n is 1 or 2; and

X and Y, together with the phenyl to which they are attached, form a ring system selected from quinolyl; 2-hydroxyquinolyl; benzothiazolyl; 2-aminobenzothiazolyl; benzoisothiazolyl; indazolyl; 3-hydroxyindazolyl; indolyl; spiro[cyclopentane-1,3′-indolinyl]; and oxindolyl; wherein said ring system may optionally be substituted with one to three substituents independently selected from ($C_1$–$C_3$) alkyl, or with one substituent selected from chloro, fluoro, benzoxazolyl, 2-aminobenzoxazolyl, benzoxazolonyl, 2-aminobenzoxazolinyl, benzothiazolonyl, benzoimidazolonyl, benzotriazolyl, and phenyl optionally substituted with one chloro or fluoro;

which comprises reacting a piperazine salt of the formula

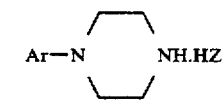

wherein Z is fluoro, chloro, bromo, iodo, methanesulfonate, trifluoromethanesulfonate, or trifluoroacetate and Ar is as defined above, with an alkyl halide containing compound of the formula

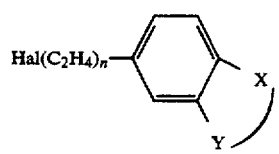

wherein n, X and Y are as defined above and Hal is fluoro, chloro, bromo or iodo, in water with an excess of reagent to neutralize the hydrohalic acid, heating the mixture under conditions which are suitable to effect the coupling of said piperazine salts with said alkyl halide containing compounds, and, if desired, preparing the corresponding pharmaceutically acceptable acid addition salt. Preferably, the mixture is heated to about the reflux temperature. Especially preferably, the compound of formula I is reacted with aqueous hydrochloric acid to form a hydrochloride monohydrate.

The optional substitution in the naphthyl and oxindolyl may be in either ring of the naphthyl and oxindolyl group, respectively. Examples of such substitutions are 6-fluoronaphthyl, 4-methoxynaphthyl, 1-ethyloxindolyl and 6-fluorooxindolyl. The optional substitution in the indanyl is in the saturated ring of the indanyl group. Preferred substitution of the oxindolyl by $(C_1-C_3)$alkyl is by one to three methylene groups, or one ethyl.

Preferred compounds for use in the process of the present invention are those wherein n is 1, those wherein X and Y together with the phenyl to which they are attached form oxindolyl and those wherein Ar is naphthyl or benzoisothiazolyl.

A specific preferred compound which may be prepared in accordance with the present invention is 5-(2-(4-(1,2-benzisothiazol-3-yl)-1-piperazinyl)ethyl)-6-chloro-1,3-dihydro-2H-indol-2-one hydrochloride monohydrate.

DETAILED DESCRIPTION OF THE INVENTION

Generally, the process of the invention is effected in the presence of a neutralizing agent, for example, a base and including but not limited to alkali or alkaline earth metal carbonates such as sodium carbonate or potassium carbonate; bicarbonates such as sodium bicarbonate; hydrides and tertiary amines such as triethylamine or diisopropylethylamine.

Both the piperazine salts and the alkyl halide containing compounds are referred to herein as substrates. For the purposes of the present invention, the substrates can be present in equal molar amounts or one substrate can be present in excess.

In a preferred embodiment, the process of this invention involves the use of from about one to five molar equivalents of a neutralizing agent based on the substrate not present in excess with from about three to ten volumes of water based on the weight, e.g. grams, of the substrate not present in excess.

In a more preferred embodiment, the process of this invention involves the use of about three molar equivalents of a neutralizing agent based on the substrate with about five volumes of water based on the weight, e.g. grams, of the substrate which is not present in excess. In a further preferred embodiment, the neutralizing agent is sodium carbonate.

The piperazine salt derivative is substantially soluble, and the alkyl halide derivative is substantially insoluble in water. The mixture of these materials is heated for a time sufficient to allow the reaction to proceed, generally at least about 8 to 12 hours, and preferably for at least 10 to 12 hours. The reaction is generally conducted at a temperature of from about 80°-100° C., and preferably at the reflux temperature of the reaction mixture including solvent. The reflux temperature will generally be about 100° C. The flask is cooled generally to about room temperature (20°-25° C.) or below but not to freezing and the product is filtered off. This reaction has not shown formation of byproducts.

The pharmaceutically acceptable acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic, such as methanesulfonic, benzenesulfonic, and related acids.

The monohydrate may be prepared by reacting anhydrous 5-(2-(4-(1,2-benzisothiazol-3-yl)-1-piperazinyl)ethyl)-6-chloro-1,3-dihydro-2H-indol-2-one with aqueous hydrochloric acid. In general, this reaction takes place at temperatures of from about room temperature to about 100° C., usually from about 60° to about 65° C. Depending on the reaction temperature and other conditions, the reaction time generally ranges from about 2 hours to about 48 hours, conveniently about 3 to 24 hours. The concentration of the hydrochloric acid in the reaction solution ranges from about 0.3 to about 3.0M, and preferably about 0.7M.

The neuroleptic activity of the compounds prepared by the process of this invention makes them useful for treating psychotic disorders in human subjects. For example, these compounds are useful for treating psychotic disorders of the schizophrenic types, and in particular the compounds are useful for removing or ameliorating such symptoms as anxiety, agitation, excessive aggression, tension, and social or emotional withdrawal in psychotic patients.

The neuroleptic compounds of formula I and their pharmaceutically acceptable salts (hereafter also referred to as the "active compounds"), can be administered to a human subject either alone, or, preferably, in combination with pharmaceutically-acceptable carriers or diluents, in a pharmaceutical composition, according to standard pharmaceutical practice. A compound can be administered orally or parenterally. Parenteral administration includes especially intravenous and intramuscular administration. Additionally, in a pharmaceutical composition comprising an active compound the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use of an active compound the compound can be administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When an active compound is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances, an effective amount for treating a psychotic disorder will be a daily dosage in the range from 5 to 500 mg, and preferably 50 to 200 mg, and optionally 50 to 100 mg, in single or divided doses, orally or parenterally. In some instances it may be necessary to use dosages outside these limits.

The following examples are provided solely for the purpose of further illustration.

EXAMPLE 1

Preparation of 5-[2-[4-(1,2-benzisothiazol-3-yl)-1-piperazinyl]ethyl]-6-chloro-1,3-dihydro-2H-indol-2-one A 20-gallon glass lined tank, under a nitrogen atmosphere, was charged with 33.5 liters of water and 9.4 kilograms (kg) of sodium carbonate (dense, 89.1 moles, 3.4 eq.). The resulting mixture was stirred to give a solution. To the solution 6.4 kg of 2-chloroethyl-6-chlorooxindole (27.8 moles, 1.06 eq.) was charged, followed by 6.7 kg of 3-piperazinyl-1,2-benzisothiazole hydrochloride (26.2 moles, 1.0 eq.). This was stirred and heated to reflux (100° C.). After 11 hours the reaction was sampled for high pressure liquid chromatography (HPLC) assay. The reflux was continued for another 2 hours then the reaction was cooled to 25° C. and the slurry stirred for 1 hour. The product was observed and found to be essentially free from lumps and gummy matter. The product was collected by filtration on a 30" Lapp. A 14 liter water wash was added to the tank and cooled to 12° C. and then used to wash the product. The cake was pulled as dry as possible, and the product was returned to the tank along with 40 liters of isopropyl alcohol (IPO). This was cooled and then stirred for 2 hours and the product was collected by filtration. The cake was washed with 13.4 liters of fresh IPO, then dried under vacuum at 30° to 40° C.

After drying, 17.3 kg of the title compound was obtained. This was in excess of the theoretical weight yield due to some residual carbonate in the crude product.

EXAMPLE 2

Recrystallization of 5-[2-[4-(1,2-benzisothiazol-3-yl)-1-piperazinyl]ethyl]-6-chloro-1,3-dihydro-2H-indol-2-one To a clean and dry 100-gallon glass lined tank was charged 9.0 kg of the material obtained in Example 1 and 86 gallons of tetrahydrofuran (THF). The slurry was heated to reflux and held for 1 hour. The hazy solution was then filtered through a 14" sparkler precoated with filter aid and backed with a Fulflo filter to a clean, dry, and "spec free" glass-lined tank on a lower level. The batch was concentrated by vacuum distillation. Another 8.3 kg of the material obtained in Example 1 was dissolved in 83 gallons of THF in the upper tank. This was filtered to the lower tank. The tank lines and sparkler were rinsed with 10 gallons of THF. The batch was concentrated to about 22 gallons, then cooled to 5° C. and stirred for 1 hour. The product was collected under spec free conditions by filtration on a 30" Lapp. Then 20 gallons of fresh spec free IPO were cooled in the tank and used to rinse the product cake. The product was collected and dried under vacuum at 45° C.; yielding 9.05 kg of product (83.8% yield for the coupling and recrystallization).

The product matched the spectra of a standard NMR and showed the correct retention time by HPLC with 99.7% assay.

EXAMPLE 3

Preparation of 5-[2-[4-(1,2-benzisothiazol-3-yl)-1-piperazinyl]ethyl]-6-chloro-1,3-dihydro-2H-indol-2-one A 250 milliliter (ml) flask was charged with 25 ml of water and 6.91 grams (gm) of $Na_2CO_3$ (65.3 mmole, 3.4 eq.). The mixture was then stirred to give a solution. To the solution was charged 4.68 gm of 2-chloroethyl-6-chlorooxindole (20.35 mmole, 1.06 eq.) and 4.90 gm of 3-piperazinyl-1,2-benzisothiazole hydrochloride (19.2 mmole, 1 eq.). This was stirred and heated to reflux (approximately 100° C.). The resulting product did not become gummy or mass together. After 14 hours, the reaction was sampled for HPLC assay. The reflux was continued for another 2 hours than the reaction was cooled to about 20° C. and the slurry stirred for about 1 hour. The product was collected by filtration. The cake was pulled as dry as possible and the product was returned to the flask together with 25 ml isopropyl alcohol (IPO). The product was collected by filtration, washed with a small amount of IPO and dried under vacuum.

After drying, 7.29 gm of the title compound was obtained, representing a weight yield of 92.1%. The product matched the spectra of a standard nuclear magnetic resonance (NMR) and showed the correct retention time by HPLC with 98.6% assay.

We claim:

1. A process for preparing a compound of the formula:

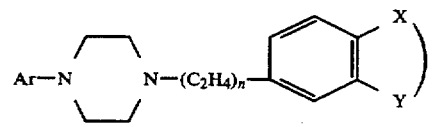

I or a pharmaceutically acceptable acid addition salt thereof, wherein

Ar is naphthyl optionally substituted with one to four substituents independently selected from fluoro, chloro, trifluoromethyl, methoxy, cyano and nitro; quinolyl; 6-hydroxy-8-quinolyl; isoquinolyl; quinazolyl; benzoisothiazolyl and an oxide or dioxide thereof, each optionally substituted with one or more substituents independently selected from fluoro, chloro, trifluoromethyl, methoxy, cyano, and nitro; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; and phthalazinyl;

n is 1 or 2; and

X and Y, together with the phenyl to which they are attached, form a ring system selected from quinolyl; 2-hydroxyquinolyl; benzothiazolyl; 2-aminobenzothiazolyl; benzoisothiazolyl; indazolyl; 2-hydroxyindazolyl; indolyl; spiro[cyclopentane-1,3'-indolinyl]; and oxindolyl; wherein said ring system may optionally be substituted with one to three substituents independently selected from $(C_1-C_3)$alkyl, or with one substituent selected from chloro, fluoro, and phenyl optionally substituted by one chloro or fluoro; benzoxazolyl; 2-aminobenzoxazolyl; benzoxazolonyl; 2-aminobenzoxazolinyl; benzothiazolonyl; benzoimidazolonyl; and benzotriazolyl;

which comprises reacting a piperazine salt of the formula

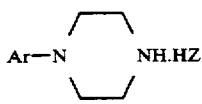

II wherein Z is fluoro, chloro, bromo, iodo, methanesulfonate, trifluoromethanesulfonate, or trifluoroacetate; and Ar is as defined above, with an alkyl halide containing compound of the formula

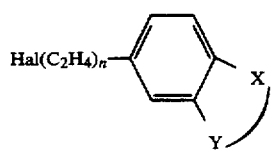

III wherein n, X and Y are as defined above and Hal is fluoro, chloro, bromo or iodo, in water with a reagent to neutralize the hydrohalic acid, heating the mixture under conditions which are suitable to effect the coupling of said piperazine salt with said alkyl halide containing compound and, if desired, preparing the corresponding pharmaceutically acceptable acid addition salt.

2. A process according to claim 1 wherein the piperazine salt is a hydrochloride or triflate salt.

3. A process according to claim 1 wherein from about one to five molar equivalents of a neutralizing agent based on the substrate not present in excess is used with from about three to ten volumes of water based on the weight of the substrate not present in excess.

4. A process according to claim 3 wherein about three molar equivalents of a neutralizing agent and about five volumes of water are used.

5. A process according to claim 4 wherein the neutralizing agent is selected from the group consisting of alkali metal carbonates, alkaline earth metal carbonates, bicarbonates, hydrides and tertiary amines.

6. A process according to claim 5 wherein the neutralizing agent is sodium carbonate.

7. A process according to claim 6 wherein the piperazine salt, alkyl halide containing compound, sodium carbonate, and water are combined and heated to reflux.

8. A process according to claim 1 wherein the mixture is heated to about reflux temperature.

9. A process according to claim 8 wherein the temperature of reflux is about 100° C.

10. A process according to claim 1 wherein the compound of the formula I is 5-(2-(4-(1,2-benzisothiazol-3-yl)-1-piperazinyl)ethyl)-6-chloro-1,3-dihydro-2H-indol-2-one.

11. A process according to claim 10, comprising the step of reacting the compound of formula I with aqueous hydrochloric acid to form 5-(2-(4-(1,2-benzisothiazol-3-yl)-1-piperazinyl)ethyl)-6-chloro-1,3-dihydro-2H-indol-2-one hydrochloride monohydrate.

12. A process according to claim 1 which comprises reacting the piperazine salt with the alkyl halide containing compound in water and a neutralizing agent; refluxing the mixture for at least about 8 to 16 hours; cooling the mixture and filtering off the product.

13. A process according to claim 12 wherein from about one to five molar equivalents of a neutralizing agent based on the substrate not present in excess is used with from about three to ten volumes of water based on the weight of the substrate not present in excess.

14. A process according to claim 13 wherein about three molar equivalents of a neutralizing agent and about five volumes of water are used.

15. A process according to claim 14 wherein the neutralizing agent is sodium carbonate.

16. A process according to claim 15 wherein the piperazine salt, alkyl halide containing compound, sodium carbonate and water are combined and heated to reflux.

17. A process according to claim 16 wherein the temperature of reflux is about 100° C.

18. A process according to claim 12 wherein the compound of formula I is 5-(2-(4-(1,2-benzisothiazol-3-yl)-1-piperazinyl)ethyl)-6-chloro-1,3-dihydro-2H-indol-2-one.

19. A process according to claim 18 comprising the step of reacting the compound of formula I with aqueous hydrochloric acid to form 5-(2-(4-(1,2-benzisothiazol-3-yl)-1-piperazinyl)ethyl)-6-chloro-1,3-dihydro-2H-indol-2-one hydrochloride monohydrate.

* * * * *

UNITED STATES PATENT AND TRADEMARK OFFICE
CERTIFICATE OF CORRECTION

PATENT NO. : 5,338,846
DATED : 8/16/94
INVENTOR(S) : F. R. Busch et al

It is certified that error appears in the above-identified that said Letters Patent is hereby corrected as shown below:

On the title page, item [75] Inventors: should read as follows:

--[75] Inventors: Frank R. Busch, Gales Ferry; Paul Bowels, Groton; Douglas J. M. Allen, New London; Sabeto A. DiRoma, Uncasville; Dennis M. Godek, Glastonbury; all of Conn.--.

Signed and Sealed this

Eleventh Day of April, 1995

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,338,846
DATED : Aug. 16, 1994
INVENTOR(S) : F. R. Busch et al

It is certified that error appears in the above-indentified patent and that said Letters Patent is hereby corrected as shown below:

On the title page, item [75] Inventors: should read as follows:

--[75] Inventors: Frank R. Busch, Gales Ferry; Paul Bowles, Groton; Douglas J. M. Allen, New London; Sabeto A. DiRoma, Uncasville; Dennis M. Godek, Glastonbury; all of Conn.--.

This certificate supersedes Certificate of Correction issued April 11, 1995.

Signed and Sealed this

Twenty-seventh Day of February, 1996

Attest:

BRUCE LEHMAN

*Attesting Officer*   *Commissioner of Patents and Trademarks*